United States Patent [19]

Michaelis et al.

[11] 4,310,454
[45] Jan. 12, 1982

[54] NOVEL ORGANO-TIN COMPOUNDS

[75] Inventors: Klaus-Peter Michaelis, Lindenfels; Horst Müller, Fürth, both of Fed. Rep. of Germany

[73] Assignee: Ciba-Geigy Corporation, Ardsley, N.Y.

[21] Appl. No.: 134,724

[22] Filed: Mar. 27, 1980

[30] Foreign Application Priority Data

Apr. 3, 1979 [CH] Switzerland ............. 3090/79

[51] Int. Cl.³ .............................. C08K 5/57
[52] U.S. Cl. ...................... 260/45.75 S; 260/429.7
[58] Field of Search ................ 260/429.7, 45.75 S

[56] References Cited

U.S. PATENT DOCUMENTS 2,731,482 1/1956 Stefl et al. ............ 260/429.7
2,731,484 1/1956 Best ..................... 260/429.7
2,870,119 1/1959 Leistner et al. ....... 260/429.7 X
2,891,922 6/1959 Johnson ................ 260/429.7
2,914,506 11/1959 Mack et al. ........... 260/429.7

OTHER PUBLICATIONS

Sawyer, Organotin Compounds, Marcel Dekker Inc., N.Y., p. 381, (1971).

Primary Examiner—Helen M. S. Sneed
Attorney, Agent, or Firm—Harry Falber

[57] ABSTRACT

Organo-tin compounds of the formula I

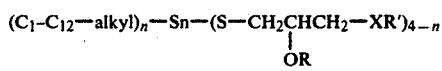

wherein n is 1 or 2, R is hydrogen or a $C_1$–$C_{18}$acyl radical, X is oxygen or sulfur, and R' is $C_1$–$C_{20}$alkyl. These compounds are stabilizers for halogen-containing polymers. The starting materials for obtaining these compounds are also claimed.

8 Claims, No Drawings

NOVEL ORGANO-TIN COMPOUNDS

The present invention relates to novel organo-tin compounds, processes for their production, their use as stabilisers for halogen-containing polymers, and the polymers stabilised therewith.

Organo-tin compounds are widely known, but they do not always satisfy the stringent demands of practice made of PVC stabilisers. It is therefore the object of this invention to provide organo-tin compounds which, compared with those of the prior art, have superior stabiliser properties, especially as regards odourlessness, processing properties at elevated temperature, heat resistance, as well as in special formulations, as e.g. a batch for test samples.

Accordingly, the invention relates to organo-tin compounds of the formula I

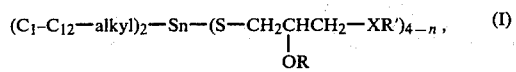  (I)

wherein n is 1 or 2, R is hydrogen or a $C_1$–$C_{18}$acyl radical, X is oxygen or sulfur, and R' is $C_1$–$C_{20}$alkyl.

In the compounds of the formula I, n can be 1 or 2, so that these will be understood to comprise monoalkyl and dialkyl tin compounds which can also exist as mixtures. It is preferred, however, that n is 1.

R as $C_1$–$C_{18}$acyl is preferably $C_1$–$C_{18}$alkanoyl, $C_7$–$C_{11}$aroyl, or also $C_4$–$C_{18}$alkoxycarbonylalkanoyl, such as benzoyl, tert-butylbenzoyl, a ($C_1$–$C_8$alkyl)-maleic acid hemiester, such as methylmaleic acid hemiester, or especially acetyl or propionyl. However, a preferred identity of R as acyl is also acetoacetyl.

X can be oxygen or sulfur, but is preferably oxygen.

R' as $C_1$–$C_{20}$alkyl is straight-chain or branched and is preferably $C_8$–$C_{20}$alkyl, such as dodecyl, tetradecyl or octadecyl. Branched radicals are especially preferred, in particular iso-octyl.

The alkyl radicals bonded to tin are preferably straight-chain and are especially methyl, n-butyl or n-octyl.

Accordingly, preferred compounds are those of the formula I wherein n is 1 or 2 and R is $C_1$–$C_{18}$alkanoyl or acetoacetyl, X is oxygen, and R' is $C_8$–$C_{20}$alkyl.

Especially preferred compounds are those of the formula I wherein n is 1 and R is acetyl, propionyl or acetoacetyl, X is oxygen, and R' is $C_8$–$C_{20}$alkyl.

The most preferred compounds are those of the formula I wherein alkyl bonded to tin is methyl, n-butyl or n-octyl, n is 1, and R is acetyl, propionyl or acetoacetyl, X is oxygen, and R' is alkyl of 8, 10, 12, 14 or 18 carbon atoms, as well as the compounds specified in the Examples and also the compounds

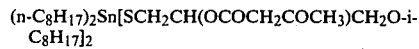

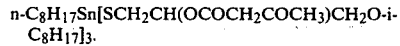

The compounds of the formula I can be obtained by methods which are known per se, e.g. from a tin halide

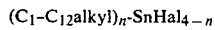

and a monothioglycerol ester of the formula II $$HS-CH_2\underset{\underset{OR}{|}}{CH}CH_2-XR',$$  (II)

wherein R, X and R' are as defined above. The reaction is carried out in a solvent, especially a two-phase solvent, such as water and an organic solvent, e.g. water/alkane, such as water/heptane, advantageously in the presence of a buffer such as sodium bicarbonate, and at slightly elevated temperature, e.g. at 30°–60° C. It is advantageous to react 1 mole of tin trihalide with 3 moles of an ester of the formula II, or 1 mole of tin dihalide with 2 moles of an ester of the formula II. It is also possible, however, to replace the tin halide wholly or partially by a corresponding tin oxide and, depending on the amount employed thereof, to obtain superbasic tin compounds, which also constitute an object of the invention.

The esters of the formula II are novel and likewise constitute an object of the present invention. R, X and R' in these compounds have the above general and preferred meanings and R is in particular acetyl, propionyl or acetoacetyl. The esters of the formula II are suitable for obtaining compounds of the formula I in the above process. They can be produced by methods which are known per se. e.g. by reacting a glycidyl ether or thioether with hydrogen sulfide and acylating the resultant monothioglycerol ether or thioether, e.g. with acetic anhydride or ethyl acetate as described in the Examples herein.

The stabilisers of the present invention are most suitable for protecting chlorinated thermoplastics against heat- and light-induced degradation. Compounds of the formula I are incorporated in the plastics material as a rule in amounts of 0.01 to 10% by weight, preferably 0.1 to 5% by weight. Accordingly, the invention also relates to thermoplastic moulding compositions containing 0.01 to 10% by weight of a stabiliser of the formula I, based on the thermoplastic moulding composition.

Examples of chlorinated thermoplastics are: polyvinylidene chloride, post-chlorinated polyolefins, and, preferably, polymers of or based on vinyl chloride, e.g. E-, S- and M-PVC, which can also be plasticised and post-chlorinated. A preferred chlorinated thermoplastic, however, is rigid PVC, from which e.g. finished parts for exterior use can be obtained by known methods such as injection moulding or extrusion.

Examples of comonomers for thermoplastics based on vinyl chloride are: vinylidene chloride, trans-dichloroethane, ethylene, propylene, butylene, maleic acid, acrylic acid, fumaric acid, itaconic acid, or vinyl acetate.

Depending on the end use, further additives can be added to the moulding composition before, during or after the addition of the stabiliser. Examples of such additives are: lubricants, preferably montan waxes or glycerol esters, fillers, reinforcing fillers, such as glass fibres, and modifiers, such as impact strength additives.

The invention is illustrated in more detail by the following Examples, in which parts and percentages are by weight.

EXAMPLE 1

5 g of solid sodium hydrogen sulfide monohydrate are saturated with hydrogen sulfide at room temperature in 250 ml of methanol. Then 186 g (1 mole) of 2-ethylhexyl glycidyl ether are added dropwise at room temperature and with efficient stirring in the course of 2 hours, while simultaneously introducing hydrogen sulfide gas. The flow of hydrogen sulfide gas is constantly introduced in an amount just sufficient for the reaction solution to take up. The temperature should not exceed 30°–40° C. in order effectively to prevent the formation of corresponding thioethers. When the reaction of the epoxide is complete, the catalyst is destroyed with a small amount of dilute sulfuric acid and the reaction mixture is extracted with ether. The ethereal extract is washed neutral with water, dried over magnesium sulfate and the solvent is removed. Distillation of the residue at 75° C./$10^{-3}$ torr yields the pure monothioglycerol 2-ethylhexyl ether with a SH content of 14.8%.

EXAMPLE 2

1 mole of the monothioglycerol ether obtained in Example 1 is diluted with 110 g of acetic anhydride. While cooling with ice water, 15 ml of conc. sulfuric acid are added dropwise to this solution. The temperature should not exceed 40° C. The batch is stirred for 1 hour, diluted with water, and then extracted with ether. The ethereal extract is washed neutral with sodium bicarbonate solution. Distillation at 85° C./$4.10^{-3}$ torr yields 3-(2-ethylhexyloxy)-2-acetoxy-1-propanethiol as an odourless oil with a SH content of 11.6%.

EXAMPLE 3

As described in Example 1, the monothioglycerol ether is reacted with propionic anhydride to produce the corresponding propionic acid ester, viz. 3-(2-ethylhexyloxy)-2-propionyloxy-1-propanethiol. The odourless product has a SH content of 10.8%.

EXAMPLE 4

220 g of the thioglycerol ether of Example 1 are reacted with 200 ml of ethyl acetate and the mixture is heated until a total amount of 50 ml of ethanol are distilled off. Non-reacted ethyl acetate is then removed in a water jet vacuum, affording in quantitative yield the acetoacetylated thioglycerol ether, viz. 3-(2-ethylhexyloxy)-2-acetoacetoxy-1-propanethiol, in the form of a colourless and odourless compound with a SH content of 9.8%.

EXAMPLE 5

The thioglycerol derivatives described in Examples 1 to 4 can be converted into the monoorganic tin mercaptides by the following general procedure. The thioglycerol derivatives are heated with the calculated equivalent amounts (based on the SH content) of mono-n-butyl-tin oxide to about 80° C. with stirring, and the water of reaction formed is stripped off in a water jet vacuum. The mono-n-butyl-tin oxide goes completely into solution except for insignificant amounts of polymer impurities which, after cooling, are removed by filtration. The mono-n-butyl-tin mercaptides are obtained in the form of clear, viscous, and completely odourless products:

|   |   | $n_D^{20}$ | IR (cm$^{-1}$) |
|---|---|---|---|
| (a) | $C_4H_9Sn(SCH_2\underset{\underset{OH}{\mid}}{C}HCH_2OCH_2CH(CH_2CH_3)CH_2CH_2CH_2CH_3)_3$ | 1.5131 | 3400 (OH) |
| (b) | $C_4H_9Sn(SCH_2\underset{\underset{OCOCH_3}{\mid}}{C}HCH_2OCH_2CH(CH_2CH_3)CH_2CH_2CH_2CH_3)_3$ | 1.500 | 1740 (CO) |
| (c) | $C_4H_9Sn(SCH_2\underset{\underset{OCOCH_2COCH_3}{\mid}}{C}HCH_2OCH_2CH(CH_2CH_3)CH_2CH_2CH_2CH_3)_3$ | 1.5038 | 1715 (enol) 1740 (CO) |

EXAMPLE 6

The thioglycerol derivatives can be converted into the diorgano-tin mercaptides by a procedure analogous to that described in Example 5. The equivalent amount (based on the SH content) of di-n-butyl-tin oxide is used and water of reaction formed at 80° C. is removed in vacuo. After filtration, the corresponding diorgano-tin mercaptides are obtained as clear, viscous, and completely odourless products:

|   |   | $n_D^{20}$ | IR (cm$^{-1}$) |
|---|---|---|---|
| (a) | $(C_4H_9)_2Sn(SCH_2\underset{\underset{OH}{\mid}}{C}HCH_2OCH_2CH(CH_2CH_3)CH_2CH_2CH_2CH_3)_2$ | 1.5103 | 3400 (OH) |
| (b) | $(C_4H_9)_2Sn(SCH_2\underset{\underset{OCOCH_3}{\mid}}{C}HCH_2OCH_2CH(CH_2CH_3)CH_2CH_2CH_2CH_3)_2$ | 1.4963 | 1740 (CO) |
| (c) | $(C_4H_9)_2Sn(SCH_2\underset{\underset{OCOCH_2COCH_3}{\mid}}{C}HCH_2OCH_2CH(CH_2CH_3)CH_2CH_2CH_2CH_3)_2$ | 1.4913 | 1715 (enol) 1740 (CO) |

EXAMPLE 7

A batch suitable for the manufacture of test samples has the following composition:

| S-PVC | 100.0 parts |
|---|---|
| paraffin wax | 0.2 part |
| calcium stearate | 1.0 part |
| organo-tin mercaptide | 0.5 part |

After the compounds were thoroughly mixed, a 1 mm sheet was prepared at 80° C. The discolouration (Yellowness Index) of the sheet was then determined:

| without stabiliser | Yellowness Index 64.4 |
|---|---|
| (a) n-C$_4$H$_9$—Sn(SCH$_2$CHCH$_2$O—i-C$_8$H$_{17}$)$_3$<br>　　　　　　　　　　│<br>　　　　　　　　　　OH | 11.2 |
| (b) (n-C$_4$H$_9$)$_2$Sn(SCH$_2$CHCH$_2$O—i-C$_8$H$_{17}$)$_2$<br>　　　　　　　　　　│<br>　　　　　　　　　　OH | 10.8 |
| (c) n-C$_4$H$_9$—Sn(SCH$_2$CHCH$_2$O—i-C$_8$H$_{17}$)$_3$<br>　　　　　　　　　　│<br>　　　　　　　　　　OCOCH$_3$ | 9.7 |
| (d) (n-C$_4$H$_9$)$_2$Sn(SCH$_2$CHCH$_2$O—i-C$_8$H$_{17}$)$_2$<br>　　　　　　　　　　│<br>　　　　　　　　　　OCOCH$_3$ | 17.7 |
| (e) n-C$_4$H$_9$—Sn(SCH$_2$CHCH$_2$O—i-C$_8$H$_{17}$)$_2$<br>　　　　　　　　　　│<br>　　　　　　　　　　OCOCH$_2$COCH$_3$ | 11.2 |
| (f) (n-C$_4$H$_9$)$_2$Sn(SCH$_2$CHCH$_2$O—i-C$_8$H$_{17}$)$_2$<br>　　　　　　　　　　│<br>　　　　　　　　　　OCOCH$_3$COCH$_3$ | 17.5 |

What is claimed is:

1. An organo-tin compound of the formula I

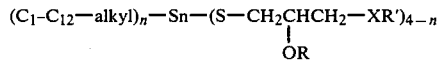

wherein n is 1 or 2, R is hydrogen or a C$_1$–C$_{18}$acyl radical, X is oxygen or sulfur, and R' is C$_1$–C$_{20}$alkyl.

2. A compound of the formula I according to claim 1, wherein n is 1 or 2 and R is C$_1$–C$_{18}$alkanoyl or acetoacetyl, X is oxygen, and R' is C$_8$–C$_{20}$alkyl.

3. A compound of the formula I according to claim 1, wherein n is 1 and R is acetyl, propionyl or acetoacetyl, X is oxygen, and R' is C$_8$–C$_{20}$alkyl.

4. A compound of the formula I according to claim 1, wherein the alkyl radical bonded to tin is methyl, n-butyl or n-octyl, n is 1, R is acetyl, propionyl or acetoacetyl, X is oxygen, and R' is C$_8$alkyl.

5. The compound

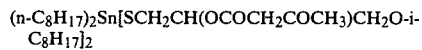

according to claim 1.

6. The compound

according to claim 1.

7. A method of stabilising chlorinated polymers which comprises incorporating into said chlorinated polymer an effective stabilizing amount of a compound of the formula I according to any one of claims 1 to 6.

8. A chlorinated polymer stabilised by an effective stabilizing amount of a compound according to any one of claims 1 to 6.

* * * * *